United States Patent
Wey (10) Patent No.: US 11,654,295 B2
(45) Date of Patent: May 23, 2023

(54) THERAPEUTIC DEVICE USING FAR-INFRARED RADIATION

(71) Applicant: Albert Chin-Tang Wey, Westmont, IL (US)

(72) Inventor: Albert Chin-Tang Wey, Westmont, IL (US)

(73) Assignee: Aldi Far-IR Products, Inc., Westmont, IL (US)

( * ) Notice: Subject to any disclaimer, the term of this patent is extended or adjusted under 35 U.S.C. 154(b) by 538 days.

(21) Appl. No.: 16/752,405

(22) Filed: Jan. 24, 2020

(65) Prior Publication Data

US 2021/0228903 A1    Jul. 29, 2021

(51) Int. Cl.
*A61N 5/06*    (2006.01)

(52) U.S. Cl.
CPC ...... *A61N 5/0618* (2013.01); *A61N 2005/066* (2013.01); *A61N 2005/0632* (2013.01)

(58) Field of Classification Search
CPC .......... A61N 5/0618; A61N 2005/0632; A61N 2005/066; A61N 5/0622; A61N 2005/0645; A61N 5/0616
See application file for complete search history.

(56) References Cited

U.S. PATENT DOCUMENTS

| | | | |
|---|---|---|---|
| 4,976,706 A | 12/1990 | Aki | |
| 5,138,133 A | 8/1992 | Sakurada | |
| 6,108,581 A | 8/2000 | Jung | |
| 6,363,285 B1 | 3/2002 | Wey | |
| 6,516,229 B1 | 2/2003 | Wey | |
| 6,531,341 B1 | 3/2003 | Peterson | |
| 6,591,142 B1 | 7/2003 | Dea | |
| 7,617,815 B2 | 11/2009 | Wey | |
| 8,285,391 B2 | 10/2012 | Malak | |
| 8,366,757 B2 | 2/2013 | Oliveira | |
| 2005/0177191 A1 | 8/2005 | Saitou | |
| 2006/0226378 A1 | 10/2006 | Yabiku | |
| 2007/0198070 A1 | 8/2007 | Oliveira | |
| 2007/0208395 A1* | 9/2007 | Leclerc | A61N 5/0616 607/86 |
| 2009/0193797 A1 | 8/2009 | Wey | |
| 2009/0312822 A1* | 12/2009 | Besner | A61N 5/06 607/100 |
| 2011/0186010 A1 | 8/2011 | Wey | |
| 2012/0061232 A1 | 3/2012 | Wey | |

(Continued)

*Primary Examiner* — Brian T Gedeon
*Assistant Examiner* — Joshua Andrew Schum-Houck
(74) *Attorney, Agent, or Firm* — IpHorgan Ltd.

(57) ABSTRACT

This invention relates to a therapeutic device for treating a human or animal body, comprising an array of infrared-emitting elements disposed on or within a flexible substrate and attached to the body part to be treated using an attachment means, said array comprising a first plurality of infrared-emitting ceramic elements having a specific spectral luminance covering at least a part of the 3-7 micrometer wavelength spectrum and having a peak wavelength between 3 and 7 micrometers, and a second plurality of infrared-emitting ceramic elements having a specific spectral luminance covering at least a part of the 7-14 micrometer wavelength spectrum and having a peak wavelength between 7 and 14, that provides an effective means to healing the body.

19 Claims, 6 Drawing Sheets

(56) References Cited

U.S. PATENT DOCUMENTS

2012/0089208 A1* 4/2012 York ............... A61N 5/0625
                                                    607/100
2017/0312539 A1* 11/2017 Wey ............... A61N 5/06
2018/0036548 A1* 2/2018 Nusse ............. A61N 2/002

* cited by examiner

THERAPEUTIC DEVICE USING FAR-INFRARED RADIATION

BACKGROUND

Field of Invention

This invention relates to a therapeutic device for treating a human or animal body, comprising a plurality of infrared-emitting ceramic elements arranged on or within a substrate for attachment to the body part to be treated. More specifically, the invention relates to a therapeutic device comprising a plurality of concave infrared-emitting ceramic elements in which 90% of the energy emitted is infrared radiation within a 3-14 μm wavelength spectrum with peak emissions within a 3-14 μm wavelength spectrum, wherein said infrared-emitting ceramic elements are arranged on or within a flexible substrate. Said therapeutic device may be used, or serve as an activating agent, for a broad range of human medical applications, from common treatment of wounds, ulcers, and pain, to more challenging medical conditions such as irritable bowel syndrome (IBD), or more severe Crohn's disease, and neurodegenerative disorders, including traumatic brain injury, stroke, dementia, Alzheimer's disease, Parkinson's disease, and amyotrophic lateral sclerosis (ALS).

Description of Prior Art

Red to infrared (R-IR) light therapy (wavelength, $\lambda$=600-1070 nm, nanometer) has been studied for years for its potential application in medicine. Hundreds of clinical studies and thousands of laboratory studies have been conducted, and some evidence suggests that R-IR light therapy has certain therapeutic benefits, such as promoting wound healing, helping to treat carpal tunnel syndrome, diminishing scars, relieving pain and inflammation, boosting immune system responses, reducing side effects of cancer treatments, and so on.

The common belief is that exposure to red or infrared light may produce a biochemical effect in cells that intensifies the activity of mitochondria, the energy-generating powerhouse of the cell. By increasing the function of mitochondria using near-infrared (NIR), for example, a cell can effectively make more adenosine triphosphate (ATP), the energy-carrying molecule found in the cells of all living things. As such, cells can operate more efficiently, revitalize themselves, and mend damage.

By the same token, light in the near-infrared range is emerging as a safe and effective therapy that is capable of arresting neuronal death. Dysfunction of mitochondria is also implicated in Alzheimer's disease, as reduced efficacy of these organelles creates reactive oxygen species (or free radicals) that lead to neuron cell death. It is thought that NIR can promote neurogenesis by exerting a hormetic effect, acting as an adaptive or positive stressor. This up-regulates our endogenous antioxidant defense system. NIR light activates cellular stress response system by targeting a key enzyme in the electron transport chain which is responsible for mitochondria-based energy production, an enzyme that is fundamental to the cellular bioenergetics of nerve cells. Thus, NIR light therapy has the potential to mitigate ubiquitous processes relating to cell damage and death, and may have applications in conditions that converge on common pathways of inflammation and oxidative stress.

Nonetheless, a major drawback of R-IR light therapy is that the light can only penetrate into the body by less than 5 mm (millimeters) beneath the skin at most. Thus, R-IR light therapy is found mainly to help reduce cosmetic skin issues, like wrinkles, psoriasis, wounds, and some side effects of chemotherapy. Equally, the biggest obstacle with infrared light therapy in neurodegenerative disease is targeting the zone of pathology deep into the brain, since there is considerable dissipation of the signal across each millimeter of brain tissue, such as the thick cranium, meninges, and brain parenchyma. Accordingly, an intracranial application of near-infrared light has to be conducted by surgically implanting an NIR optical fiber for deep brain stimulation for Parkinson's disease.

After numerous years of research in medicine with far-infrared (FIR), the present inventor discovered that FIR light therapy may provide all aforementioned benefits demonstrated by R-IR and NIR light therapy, yet surmount their problems associated with the delivery of light deep into the body.

Specifically, the proposed FIR light therapy would be superior to the R-IR and NIR light therapy over the following aspects:

1). FIR Increases Harmonic Oscillations of Molecular Bonds while R-IR and NIR Increase Anharmonic Oscillations of Molecular Bonds.

At ambient temperatures, most molecules are in their fundamental vibration energy levels (ground states). If a molecule is exposed to electromagnetic radiation that matches the frequency of one of its vibrational modes, it will absorb energy from the radiation and jump to a higher vibrational energy state.

When molecules absorb radiation at R-IR or NIR wavelengths, the electromagnetic energy is converted to anharmonic vibrations in the molecule, as overtones or combinations of its vibrational modes. (These two types of bands are the most common absorption bands in the NIR spectral region.) The molecule does not remain in its excited vibrational state for very long, but quickly releases energy to the surrounding environment in the form of heat, and then returns to the ground state. Thus, the effect of NIR absorption is heating of the tissue, since it increases the nonlinear molecular anharmonic vibrational activity. Accordingly, there is considerable dissipation of energy from R-IR and NIR sources as the light passes through the medium. As a result, the penetration depth of the light in red or near-infrared range, typically generated by a low-level laser or light emitting diode (LED), is generally about 5 mm (millimeters) or less.

In contrast, the low-intensity FIR emitted from a specifically engineered ceramic material is believed to increase the vibrations of chemical bonds in a molecule, which can be described by the harmonic/quantum model. For this model, the transition can only occur between adjacent vibrational energy levels. Furthermore, the difference between two adjacent states is always the same.

There are two distinctive features in the linear interaction of FIR photons with molecules under the harmonic/quantum model. First, the ground state of a molecule may be moved toward the dissociation limit of a chemical bond by the multiple absorption of FIR photons to higher vibrational quantum numbers. Secondly, it allows a molecule to recapture the FIR photon emitted by the other molecule, which matches the energy difference between one state and the other immediately higher energy state.

The process of absorbing and re-emitting FIR photons may be envisioned as follows. The energy from an FIR photon causes the molecule to vibrate. Some time later, the molecule gives up this extra energy by emitting another FIR photon at its original frequency (or wavelength). Once the extra energy has been removed by the emitted photon, the molecule goes back to a lower vibrational state. Much of this energy will be recaptured by other molecules.

As FIR radiation is absorbed by a molecule, the bonds in the molecule are excited to a higher state of vibration—via a variety of stretching or bending modes. More explicitly, when a molecule absorbs a photon in 3-20 micrometer wavelength range, the molecule may vibrate in six ways: symmetrical stretching, anti-symmetrical stretching, scissoring, rocking, wagging, and twisting.

After being absorbed by a molecule in human or animal body, the FIR photon may be emitted from that molecule and subsequently absorbed (or so-called "pitch-and-catch") by another molecular bond of same kind within the body, until either it is quenched or it escapes from the system. Thus, compared to R-IR and NIR photons, FIR photons may travel a much deeper into our body, providing increased therapeutic benefit without the use of invasive procedures.

2). The Role of FIR-Activated Water as a Mobile Transport Carrier

The dominant content of body fluids is water. Approximately 60-65% of body water is contained within the cells (in intracellular fluid) with the other 35-40% of body water contained outside the cells (in extracellular fluid). This fluid component outside of the cells includes the fluid between the cells (interstitial fluid), lymph and blood. Water absorbs infrared at a narrow wavelength band around 2.87 μm ($v_3$, asymmetric stretch), 3.05 μm ($v_1$, symmetric stretch), 4.65 μm ($v_2$, +$L_2$ liberations/rocking) and 6.08 μm ($v_2$, bending), which all fall in a 3-7 μm wavelength range, the so-called "Functional Group Region" in the infrared spectrum.

Naturally, hydrogen bonding interconnects several water molecules into a large cluster and causes bulk properties such as cohesion. A hydrogen bond is a specific type of dipole-dipole interaction between a partially positive hydrogen (H) atom and a partially negative electron donor that contains a pair of electrons such as oxygen (O) in water molecule (H—O—H). The strength of hydrogen bond depends on the chemical nature and geometric arrangement of each group.

The hydrogen bonds are of moderate strength, around 23 KJ/mol (compared to a covalent O—H bond at 494 KJ/mol). Meanwhile, the water molecule may absorb 6.08 μm wavelength FIR to trigger the bending of the O—H bond, with a photon energy equivalent to about 19.7 KJ/mol. The FIR photon at 6.08 μm wavelength may provide the water molecule with a comparable energy enough to overwhelm the hydrogen bond. Thus, FIR-activated water molecules are likely to break apart from a large water cluster into smaller groups by overpowering the hydrogen bonds. Consequently, smaller FIR-activated water molecule groups, along with hydrophilic compounds in the solution, have better mobility, resulting in increased circulation through the body.

On the contrary, hydrophobic groups usually have long carbon chains and do not form hydrogen bonds with water molecules. These non-polar hydrophobic groups tend to aggregate together in an aqueous environment or a polar solvent. For example, when dissolving a protein molecule in water, the protein will curl up into a ball-like shape, leaving hydrophilic groups on the outside while hydrophobic groups are buried deeply within the center. Fortunately, amino acids in protein may absorb FIR photons in three bands, 2.86-3.13 μm (for N—H symmetric and asymmetric stretch), 5.92-6.06 μm (for C═O stretch), and 6.04-6.29 μm (for N—H bend), to result in formation of smaller aggregates with increased mobility. All these bands, again, fall in aforementioned 3-7 wavelength spectrum. Therefore, absorption of FIR will make water, along with hydrophobic and hydrophilic groups dissolved within, move more freely in the body.

3). The Role of FIR in Hydrolysis of Biomolecules

Hydrolysis is any chemical reaction in which a molecule of water breaks one or more chemical bonds. Moreover, biological hydrolysis is the cleavage of biomolecules where a water molecule is consumed to prompt the separation of a larger molecule into component parts.

To give an example, peptides are short chains of amino acids linked by peptide bonds. The simplest peptides are dipeptides, while a polypeptide is a long, continuous, and unbranched peptide chain. Peptides are distinguished from proteins on the basis of size, containing approximately 50 or fewer amino acids, while proteins consist of one or more polypeptides arranged in a biologically functional way.

The hydrolysis of dipeptides gives amino acids:

$$RCH(NHP)C(O)NH(CHR')CO_2CH_3 + H_2O \rightarrow RCH(NHP)CO_2H + R'CH(NH_2)CO_2CH_3$$

As discussed above, peptides, comprising amino acids, may absorb FIR at three wavelength bands: 2.86-3.13, 5.92-6.06, and 6.04-6.29 μm, while water absorbs FIR around 2.87, 3.05, 4.65, and 6.08 μm. For that reason, irradiating the body with FIR in 3-7 μm wavelength range will promote the reaction described above.

In living systems, most biochemical reactions take place during the catalysis of enzyme. Yet, such biochemical reactions will be much enhanced in FIR environment because absorption of FIR photons causing vibrations of molecular bonds helps increasing the reaction rate. This is a classic work of Evans and Polanyi in the 1930s that illustrated the importance of molecular vibrational energy in reaction dynamics.

It was recognized early in the study of chemical kinetics that increasing the energy of reactants increased reaction rate, which was usually accomplished by simply raising the reaction temperature. However, Evans and Polanyi presented the argument that the reactant vibrational energy is the most effective at promoting reaction. As experimental techniques were refined, it became possible to demonstrate that increasing vibrational energy is indeed relatively more important than raising temperature in enhancing a molecular reaction. The expectation is that if the vibrational excitation is sufficient to raise the system to lower the activation barrier, substantial rate enhancement would be realized. (Ref.: Evans M. G. and Polanyi M., Trans. Faraday Soc., 35, P. 178, 1939)

Accordingly, it is well anticipated that irradiating with FIR in 3-7 μm wavelength spectrum will productively boost hydrolysis of proteins, fats, oils and carbohydrates in the body.

4). The Role of FIR in the Hydrolysis of Adenosine Triphosphate (ATP)

Adenosine triphosphate, also known as ATP, is a molecule that carries energy within cells. All living cells require a continual supply of energy for two main purposes: the biosynthesis of micro and macromolecules, and active transport of ions and molecules across cell membranes. In the human body, the energy derived from the oxidation of nutrients is not used directly, but it is channeled into a special energy-storage molecule, adenosine triphosphate (ATP).

ATP is stable in aqueous solutions between PH 6.8 and 7.4, in the absence of catalysts. At more extreme PH's, it rapidly hydrolyzes to ADP and phosphate. In the context of biochemical reactions, the P—O—P bonds are frequently referred to as "high-energy bonds." When ATP is hydrolyzed and converted to adenosine diphosphate (ADP), energy is released.

ATP can undergo hydrolysis in two ways:

(where R=adenosyl)

Or, it can be rewritten in abbreviated equations as:

(where ADP=adenosine diphosphate; AMP=adenosine monophosphate; $P_i$=phosphate; and $PP_i$=pyrophosphate).

The hydrolysis of ATP into ADP and inorganic phosphate ($P_i$) releases 30.5 kJ/mol of enthalpy, with a change in free energy of 3.4 kJ/mol.

The infrared absorption bands of ATP in above reaction are: P—O—P bond stretch at 9.75-11.48 μm and P=O bond stretch at 8.33-9.09 which fall in the so-called "Fingerprint Region" in infrared spectrum that spans 7-20 μm wavelength range. Absorption of FIR photons in that wavelength band may contribute about 11-15 KJ/mol to the reaction process, which may be significant.

Evidently, in order to achieve a more efficient hydrolysis of ATP, a second FIR source covering 7-14 μm wavelength band for exciting P=O and P—O—P bonds would be needed, in addition to the primary FIR source covering 3-7 μm wavelength band that excites H—O—H bonds and all other molecular bonds in Functional Group Region in infrared spectrum.

Under FIR influence, hydrolysis of ATP can effectively provide energy to drive many processes in living cells, including muscle contraction, nerve impulse propagation, and chemical synthesis. With increased energy derived from ATP, cells can operate more efficiently, rejuvenate themselves, and repair damage, in the same manner as being demonstrated with near-infrared light therapy.

5). FIR-Activated Adenosine Triphosphate (ATP) in Living Cells

All living things use ATP. ATP, best known as a universal fuel inside living cells, also serves as a molecular signal that affects cell behavior. In addition to being an essential energy source inside cells, ATP also carries critical message between cells, being used in signal transduction pathways for cell communication. For example, cells may be given signals to grow, metabolize, differentiate into specific types, or even die. That dual role is suggesting fresh ideas for fighting human diseases.

For instance, ATP signaling may result in protective and healing response, including activating blood platelets for forming a clot to stop bleeding from a new wound. A similarly promising therapeutic area is the digestive system. ATP sent from intestinal nervous system to the intestinal wall acts on P2X and P2Y receptors to control the rhythmic contractions that move food through the tract. Thus, FIR may be used as potential treatments for irritable bowel syndrome (IBS) and its more severe form, Crohn's disease.

Furthermore, ATP may be one of the body's natural cancer-fighting tools. (Eliezer Rapaport first described a tumor-killing effect of ATP in 1983). ATP signaling acts in part to promote apoptosis of the tumor cells and in part to promote cell differentiation, which slows tumor cell proliferation. Laboratory works have shown that ATP can inhibit the growth of tumors, including prostate, breast, colorectal, ovarian and esophageal cancers, and melanoma cells.

As mentioned above, in order to effectively activate ATP with far infrared, it is necessary to target two wavelength ranges: a primary 3-7 μm wavelength band for exciting most functional groups in ATP and a secondary 7-14 μm band for exciting P=O and P—O—P bonds. Thus, exposure to FIR radiation, simultaneously but separately with a primary 3-7 μm and a secondary 7-14 μm radiation sources, may change the biochemical behavior of ATP molecules and offer unusual opportunities to improve human health.

Having said that, numerous FIR therapeutic devices developed over the years for improving human health have only shown limited effect. The key problem associated with these devices is that they do not focus on the biochemical mechanisms governing how chemical compounds in the body react with cells and organisms under the influence of far infrared.

As discussed above, a primary 3-7 μm wavelength band, the so-called "Functional Group Region" in the infrared spectrum, is strongly required to excite O—H and C—H bonds, which are common in biological molecules. Other important bonds in this part of infrared spectrum also include N—H (amines and amide), C=O (ketones, amides, carboxylic acid), C=C (benzene ring), C—O (alcohol, ether), $NO_2$ (nitro compound), and the like. Many substances that are normally present in blood also have similar bonds.

In view of the above, it is believed that an additional secondary FIR source for providing the supplementary 7-14 μm wavelength band, in so-called "Fingerprint Region" of the infrared spectrum, would be helpful to excite the critical P=O and P—O—P bonds in ATP, as disclosed herein. Furthermore, FIR in the 7-14 μm wavelength range may also cover another important absorption peak at 9.39 μm for glucose and fructose, in addition to their major peaks in the Functional Group Region at 3.52, 4.24, 6.05 and 6.84 μm. By doing so, it helps the hydrolysis of polysaccharides to soluble sugar, a process called "saccharification".

Unfortunately, most FIR therapeutic devices suggested to date, including, for example, U.S. Pat. Nos. 8,285,391, 9,962,441, 10,245,444, and US Pat. Appl. No. 20190201714, all lack the primary wavelength band of 3-7 μm and seriously fall short by focusing only on the auxiliary 8-12 μm wavelength band.

Based on above discussion, the present inventor has discovered a new approach using an array of IR-emitting ceramic elements in an attachment means for enhanced IR healing effect on human or animal body by simultaneously employing two separate FIR elements, one being covering the primary 3-7 μm and the other covering the secondary 7-14 μm wavelengths, that differs from all therapeutic devices disclosed in prior art.

OBJECTS AND ADVANTAGES

Accordingly, one object of this invention is to provide a therapeutic device with amplified infrared emission in the two desirable wavelength bands, 3-7 μm and 7-14 μm, simultaneously but from two separate radiation sources;

Another object of the present invention is to provide a therapeutic device for effectively increasing the IR healing effects on human or animal body;

Also, another object of the present invention is to provide a simple, easy-to-use, and maintenance-free therapeutic device that is flexible to attach to any part of human or animal body that requires treatment.

These objectives are achieved by a therapeutic device comprising an array of IR-emitting elements. Said IR-emitting element is an IR-emitting ceramic plate made of essentially a mixture of selected IR-emitting metal oxides having specific spectral luminance covering at least a part of 3-14 μm wavelength spectrum. Said array of IR-emitting elements can be secured in a flexible attachment means and placed at close proximity of the body part that requires treatment.

Other objects, features, and advantages of the present invention will hereinafter become apparent to those skilled in the art from the following description.

SUMMARY OF THE INVENTION

In accordance with the present invention a therapeutic device comprises an array of IR-emitting elements in an attachment means that follows the contour of the body part to be treated, said IR-emitting element being an IR-emitting ceramic plate made of a mixture of IR-emitting oxides having specific spectral luminance covering at least a part of 3-14 μm (micrometer) wavelength spectrum, and more specifically, said array comprising at least first and second infrared-emitting elements, the first infrared-emitting element being a first ceramic element having a first specific spectral luminance covering at least a part of the 3-7 micrometer wavelength spectrum, the second infrared-emitting element being a second ceramic element having a second specific spectral luminance covering at least a part of the 7-14 micrometer wavelength spectrum, the second specific spectral luminance being different from the first specific spectral luminance and the second peak wavelength being different from the first peak wavelength, that provides an effective means to healing human or animal body. A locally administrable heating means may be used to provide localized heating for escalated healing effects.

DETAILED DESCRIPTION OF THE INVENTION

The therapeutic device of the present invention comprises an array of IR-emitting elements in an attachment means that follows the contour of the body part to be treated, said IR-emitting element being an IR-emitting ceramic elements made of a mixture of IR-emitting oxides. In one embodiment of the invention, the ceramic elements emit infrared radiation having a specific spectral luminance covering at least a part of 3-14 μm wavelength spectrum. In another embodiment, the array comprises at least two types of IR-emitting elements, wherein a first set of elements have a specific spectral luminance covering at least a part of the 3-7 μm wavelength spectrum, while a second set of elements have a specific spectral luminance covering at least a part of the 7-14 μm wavelength spectrum.

"Specific spectral luminance" is a term of art in the field of engineered ceramics. The term refers to the band of wavelengths of photons emitted by the ceramic element, in which most of the energy is emitted. The spectral luminance is therefore defined by a minimum wavelength $\lambda_1$ and a maximum wavelength $\lambda_2$. As a general rule in the field, engineered ceramics are typically designed such that 90% of the emitted energy falls within the band between $\lambda_1$ and $\lambda_2$. Thus, as used herein, the term "specific spectral luminance" refers to the band of wavelengths defined by a minimum wavelength ($\lambda_1$) and a maximum wavelength ($\lambda_2$) in which at least 90% of the energy is emitted by an infrared-emitting element.

The wavelength band between $\lambda_1$ and $\lambda_2$ in engineered ceramics is typically narrow. This is because ceramics are designed for specific applications at particular wavelengths, and it is necessary to provide the strongest emissions in the desired wavelengths for maximum effect. If the spectral luminance profile is broadened, then more of the energy will be emitted in undesired wavelengths, reducing the effectiveness of the device. The literature and the prior art in the field of engineered ceramics often use significantly broader ranges, such as 3-20 μm, to make generalized observations of applications using "far-infrared" radiation. However, any person of skill in the art understands that an actual engineered ceramic intended for any useful purpose will have a significantly narrower spectral luminance profile.

FIGS. 1-6 shows a first embodiment of the present invention, in which ten IR-emitting ceramic elements 12 and 13 are embedded in a substrate 11, which may be made from silicone (polydimethylsiloxane), zinc sulfide, sodium chloride, potassium bromide, or similar material. The substrate 11 is a substantially flat sheet which includes a number of pockets 18, which are curved protrusions dimensioned to contain IR-emitting elements 12 and 13. In this embodiment, all pockets 18 have the same dimension because IR-emitting elements 12 and 13 have the same dimensions. In other embodiments, however, pockets 18 may have different sizes or shapes tailored to specific applications or arrangements of IR-emitting elements 12 and 13.

Figure 1:
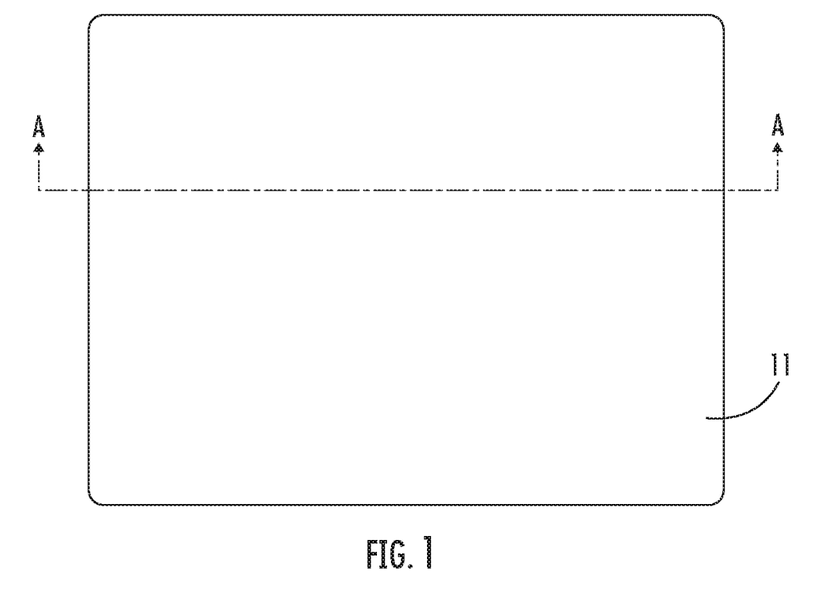
FIG. 1 is a top view of a first embodiment of the present invention showing an array of first and second IR-emitting elements embedded within a substrate.

In a preferred embodiment, the array may comprise ten IR-emitting elements arranged in row of three first IR-emitting ceramic elements 12 followed by a row of two second IR-emitting ceramic elements 13, and repeated. Preferably, the first and second IR-emitting elements 12 and 13 are spaced evenly in order to more uniformly distribute the FIR. However, other configurations of the array are within the scope of the invention. The array of IR-ceramic elements disposed in a flexible substrate 11 may be wrapped around the body part that requires treatment.

Figure 2:
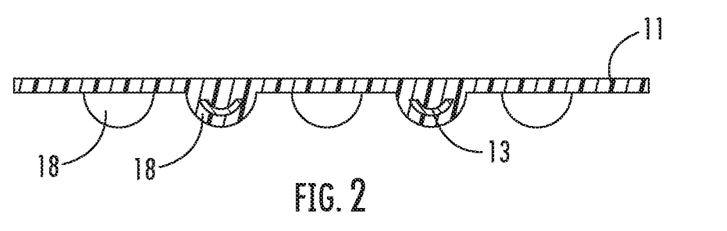
FIG. 2 is a section view of FIG. 1 taken along the line A-A showing two of the second IR-emitting elements embedded within the substrate.
Figure 3:
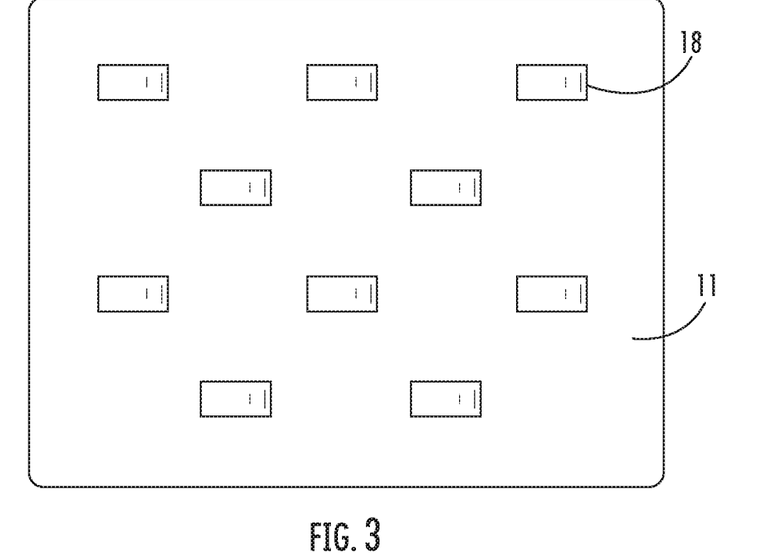
FIG. 3 is a bottom view of the array and substrate of FIG. 1.
Figure 4:
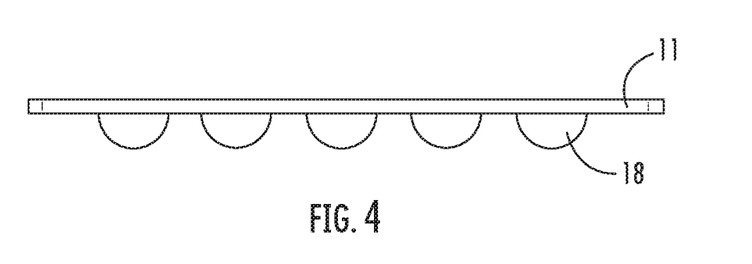
FIG. 4 is a side view of the array and substrate of FIG. 1.
Figure 5:
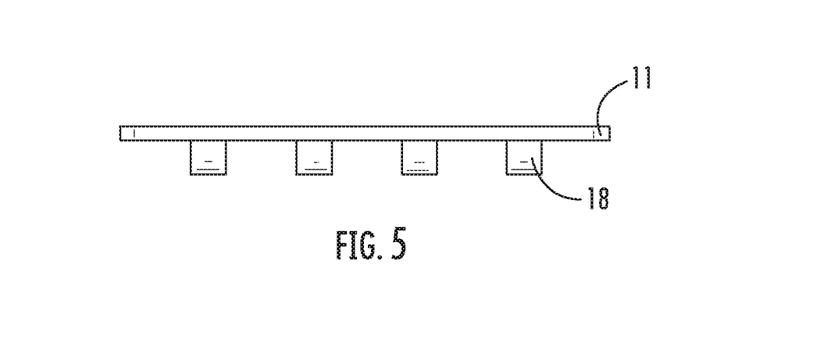
FIG. 5 is a front view of the array and substrate of FIG. 1.
Figure 6:
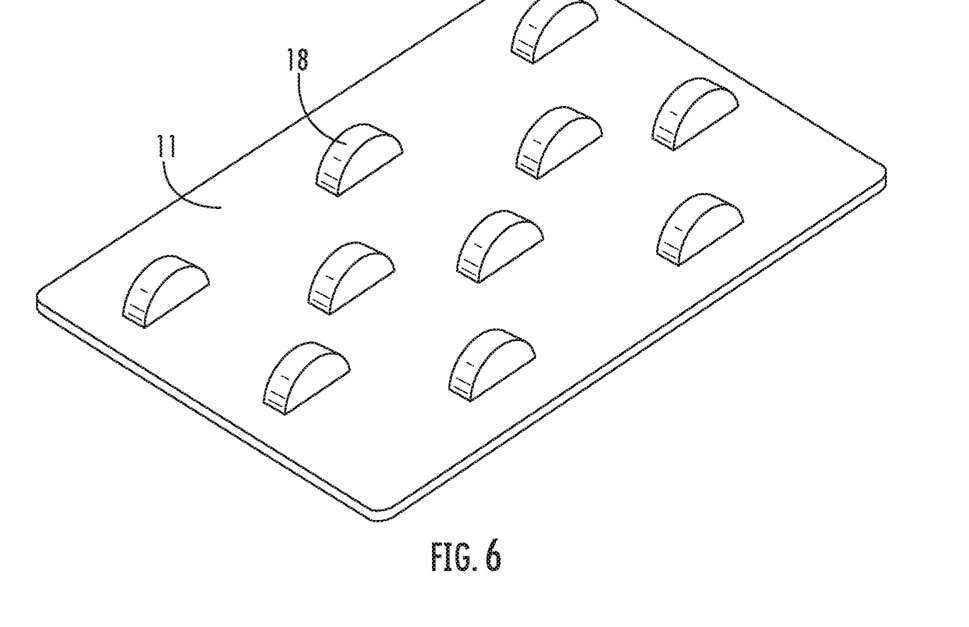
FIG. 6 is a bottom perspective view of the array and substrate of FIG. 3.

Because the IR-emitting elements 12 and 13 are embedded within the substrate 11, they are normally hidden from view. FIG. 2 shows a section view of the substrate 11, taken along line A-A. As the section view shows, the first and second IR-emitting elements 12 and 13 are disposed within pockets formed in the substrate 11. In FIG. 2, the first row of two of the second IR-emitting elements 13 are shown. The other three pockets depicted in FIG. 2 hold the first row of the first IR-emitting elements 12, which are obscured from view.

Figure 7:
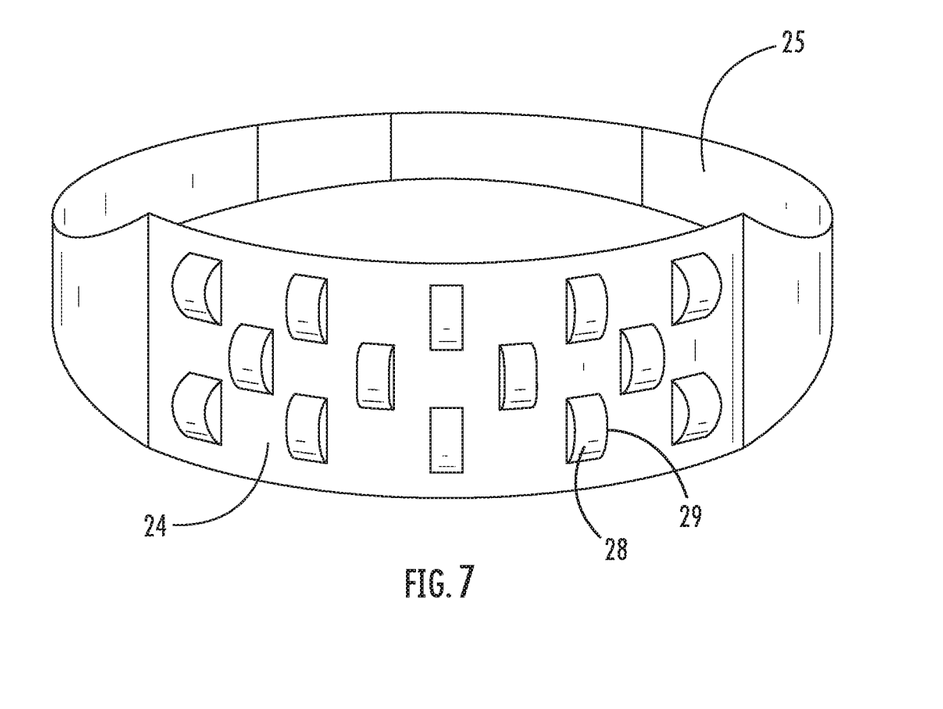
FIG. 7 is a perspective view of a second embodiment of the invention, showing an array of IR-emitting elements embedded within a substrate and disposed within an attachment means.

FIG. 7 shows a second embodiment of the invention in which a substrate 21 is enclosed within an attachment means. Preferably, the attachment means comprises an encasement 24 and straps 25 attached to both ends of the encasement 24. In the embodiment shown in FIG. 7, the encasement 24 includes holes 29 formed in one side. The holes 29 are dimensioned and positioned to allow pockets 28 of the substrate 21 to partially protrude outside the encasement 24 such that the encasement 24 is substantially flat. However, other configurations are also within the scope of the invention, such as encasements lacking holes.

The IR-emitting ceramic elements of the present invention may be formed into various shapes and sizes, depending upon the particular application. In at least one embodiment, the IR-emitting elements may be circular in shape, and may be a 2-50 mm diameter circle with a thickness of 1-10 mm. In another embodiment, the IR-emitting elements may be rectangular, having dimensions of a 2 by 3 mm rectangle to a 40 by 50 mm rectangle, with a thickness of 1-10 mm. Rectangular and circular shaped ceramics are generally easier to fabricate than other shapes.

Nonetheless, it may be advantageous to form the infrared-emitting ceramic elements with a concave shape. As it can be appreciated, each of the IR-emitting elements 12 and 13 emit infrared radiation in all directions. It is anticipated that a concave surface will help focus the rays of infrared radiation emitted by the ceramic element in a region or point at a distance from the surface of the therapeutic device. The focused radiation would penetrate the body with less attenuation than unfocused rays from a ceramic with a flat surface, and would thereby provide an increased therapeutic effect compared to flat ceramics of similar mass and dimensions. The concave surface may take a variety of shapes, such as hemispherical, bowl-shaped, or a partial cylinder.

Figure 11:
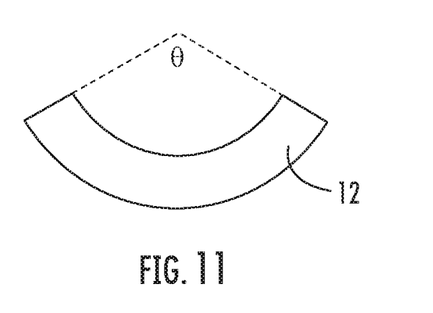
FIG. 11 is a front view of a first IR-emitting element according to the first embodiment of the invention.
Figure 12:
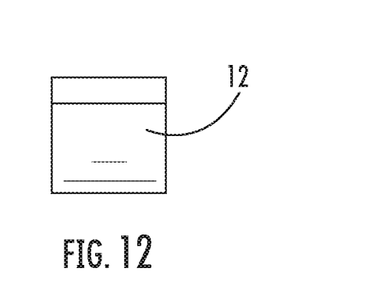
FIG. 12 is a side view of the first IR-emitting element of FIG. 11.
Figure 13:
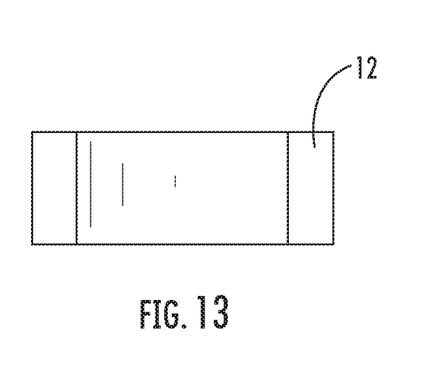
FIG. 13 is a top view of the first IR-emitting element of FIG. 11.
Figure 14:
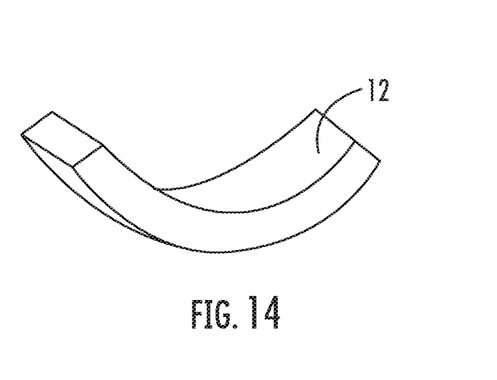
FIG. 14 is a perspective view of the first IR-emitting element of FIG. 11.

FIGS. 11-14 show a preferred embodiment, in which the IR-emitting elements 12, 13 have a partial cylindrical shape. Preferably the IR-emitting elements formed as cutout of a cylindrical tube having an angle θ as shown in FIG. 11. Preferably, the angle θ is 120°, although other angles are contemplated. The partial-cylindrical shaped ceramic element is arranged to have the concave surface facing toward the body part to be treated. This arrangement helps to focus FIR radiation at about one (1) inch above the surface of the device. When the device is wrapped closely around the body during use, the radiation will be focused to a depth of about one inch into the body tissue, and thus significantly enhance the FIR effect in the body.

Figure 8:
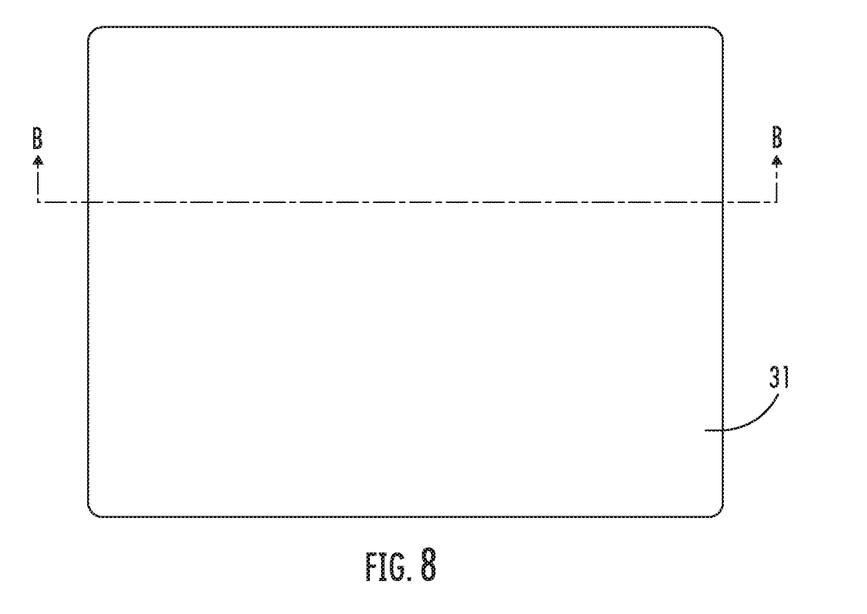
FIG. 8 is a top view of a third embodiment of the present invention showing an array of first and second IR-emitting elements embedded within a substrate.
Figure 9:
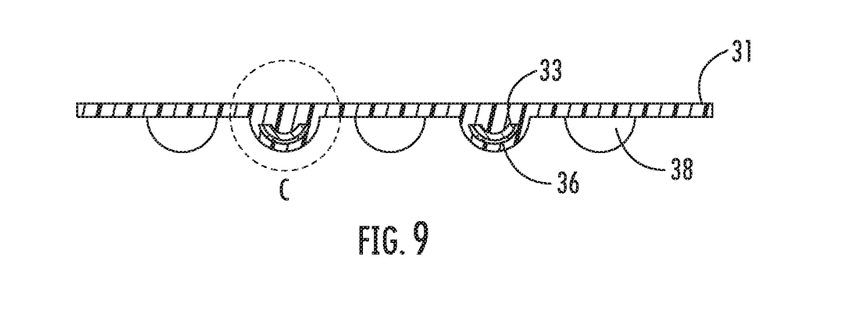
FIG. 9 is a section view of FIG. 8 taken along the line B-B showing two of the second IR-emitting elements embedded within the substrate.
Figure 10:
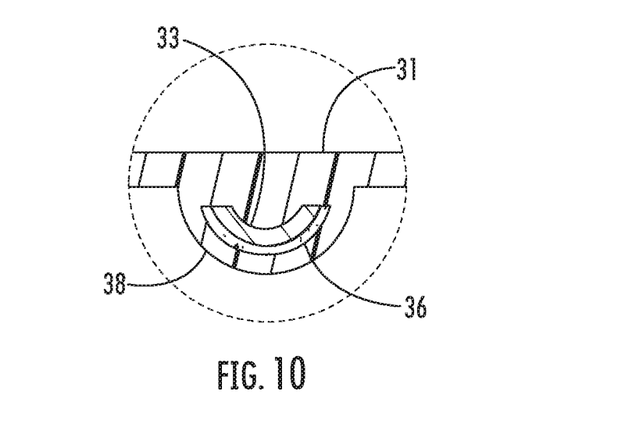
FIG. 10 is a detail view of one of the second IR-emitting elements of FIG. 9, showing the IR reflection means.

FIGS. 8-10 show a third embodiment of the present invention, further comprising an infrared reflection means 36. The infrared reflecting means 36 may be a metallic film, sheet, mesh, or coating that is capable of reflecting a substantial portion of incident infrared radiation. The infrared reflecting means is disposed behind the array of IR-emitting ceramic elements 32 and 33. The infrared reflecting means may either be a separate element, disposed between the array of elements 32 and 33 and the substrate 31, or it may be integrated or otherwise embedded inside the substrate 31. The IR reflection means 36 helps to reflect the FIR that otherwise radiates from the convex surface of the IR-emitting element toward the back of the device. Without the FIR reflection means 36, half of the FIR generated by IR-emitting elements 32 and 33 would be useless and wasted.

Figure 15:
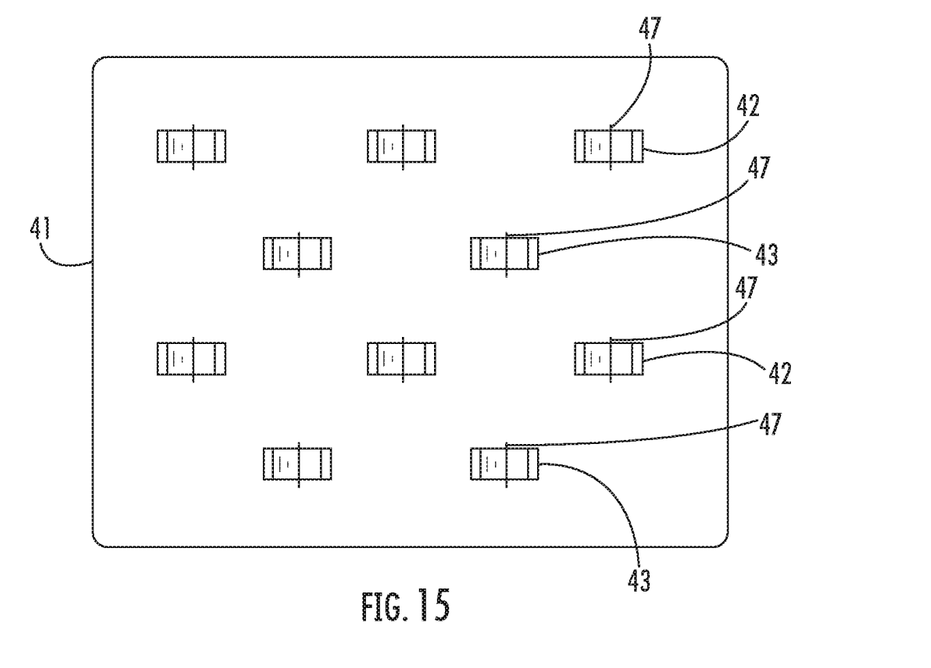
FIG. 15 is a top view of a fourth embodiment of the present invention, showing an array of first and second IR-emitting elements disposed on top of a substrate and attached to the substrate via wires.
Figure 16:
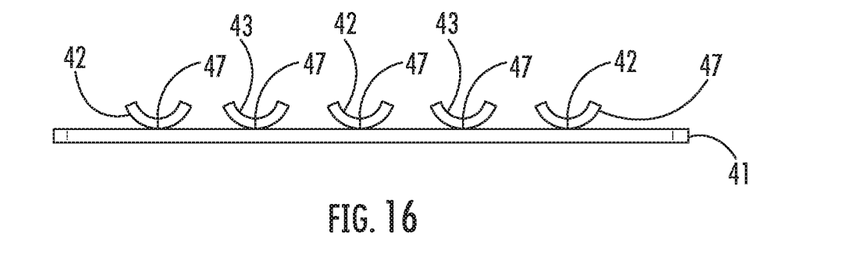
FIG. 16 is a side view of the array and substrate of FIG. 15.
Figure 17:
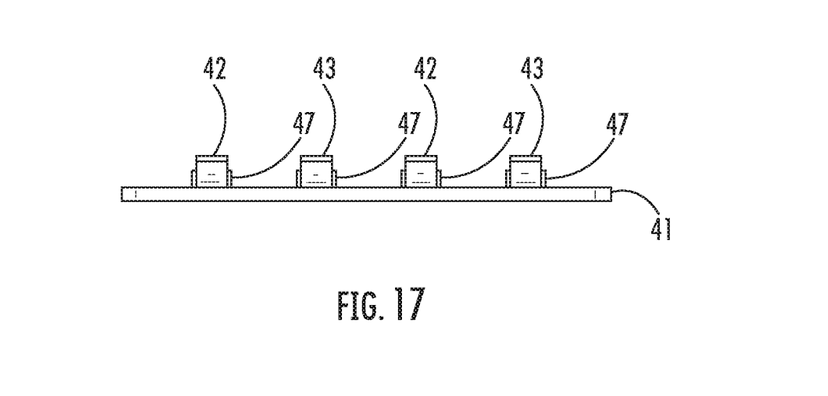
FIG. 17 is a front view of the array and substrate of FIG. 15.

FIGS. 15-17 show a fourth embodiment of the present invention, in which the IR-emitting elements 42 and 43 are disposed on top of a substantially flat, flexible substrate 41. In this embodiment, the IR-emitting elements and are attached to the substrate 41 via wires 47 to maintain the array formation. In other embodiments, wires 47 may be substituted with other means for attaching the IR-emitting elements, such as strings or adhesive.

The embodiments of the invention described thus far are passive devices. The IR-emitting ceramic elements 12 and 13 absorb ambient radiation heat and convert the heat into FIR photons. FIR radiation from the IR-emitter 12 and 13 will last indefinitely, wherever the ambient temperature is greater than Absolute Zero (i.e. 0 deg. K or −273 deg. C.). Obviously, body heat is a natural heat source for IR-emitters. However, another embodiment of the device may be an active device, comprising an external heat source, such as an electrically powered heater. The external heat source may be used in the case that both intensified FIR emission and shorter FIR wavelengths are required for accelerated healing. When heated, the peak wavelengths and spectral luminance of IR-emitters 12 and 13 will displace toward shorter wavelengths as temperature increases.

The specific spectral luminance profile and peak wavelengths emitted by an IR-emitting ceramic composite are influenced not only by the composition, but also by the processing parameters involved, such as temperature and duration of heating and cooling cycles and particle size. In order to simplify the fabrication of new IR-emitting ceramics, the present inventor has developed a base mixture of materials that provides a standardized platform for easy modification. Rather than choosing individual materials and processing parameters for each new ceramic, one may merely alter the weight percentages of key elements in the composite system. In particular, the percentages of ferric oxide, chromic oxide, cobalt oxide, and minority oxides may be altered to tailor the spectral profile.

The IR-emitting ceramic elements of the present invention can be fabricated by the following process. First, prepare a mixture of powders of IR-emitting metal oxides, such as disclosed in U.S. Pat. Nos. 6,363,285, 6,516,229, and 7,617,815 by the present inventor, in theoretical percentages by weight for intended peak wavelength and spectral luminance. An effective amount of pyroelectric material may be added to the mixture for amplified IR emissions. The pyroelectric material, tourmaline in the present invention, may be any of 5-40% by weight. Lastly, the mixture of metal oxides and pyroelectric material, along with bonding agents, catalysts, and stabilizers, is press-molded to the desired shapes and sintered in a furnace at a temperature of 1100 deg. C. or above. Several samples were prepared accordingly for concept-demonstrating experiments of the present invention.

The base mixture of IR-emitting oxides contain, by weight, 20% silicate, 20% alumina, 24% zirconia, 4% sodium monoxide, 3% potassium oxide, 3% ferric oxide, 5% chromic oxide, 4% cobalt oxide, 2% all other minority oxides, and 15% tourmaline. While the base ingredients generally provide FIR emissions, the key elements that collectively control peak wavelength and spectral luminance are: ferric oxide, chromic oxide, cobalt oxide, and nickel oxide. For example, increasing the weight percentage (wt. %) of CoO or NiO helps enhance emissions at lower wavelengths in the 3-7 µm range. Replacing the CoO with $Fe_2O_3$ and $Cr_2O_3$ may move the peak wavelength and spectral luminance toward longer wavelengths in the 7-14 µm range. Thus, various samples with distinctive wt. % of aforementioned ingredients in base mixture were made for a tailored peak wavelength and specific spectral luminance profile.

Two sample compositions were made by varying the wt. % of oxides in the base mixture. Each of the samples contains 20% silicate, 20% alumina, 24% zirconia, 4% sodium monoxide, 3% potassium oxide, and 2% minority oxides. However, Sample-1 comprises less ferric oxide and chromic oxide than the base compound, with the difference made up by adding CoO and/or NiO, while Sample-2 comprises less CoO and NiO than the base compound. The results are displayed in Table 1 below.

TABLE 1

Peak Wavelength and Spectral Luminance of Sample Ceramic Compositions

| Sample | Sample-1 | Sample-2 |
| --- | --- | --- |
| Peak Wavelength (µm) | 4 | 7 |
| Spectral Luminance (µm) | 3-7 | 7-14 |
| Wt. % $Fe_2O_3$ | 2 | 5 |
| Wt. % $Cr_2O_3$ | 4 | 5 |
| Wt. % CoO | 3 | 2 |
| Wt. % NiO | 3 | 0 |

It should be appreciated from the results of Table 1 that the spectral luminance profile may be significantly shifted by modifying the weight percentages of a few oxides in the base composition. It should also be appreciated that Sample-1 would play a primary role on therapeutic treatment of a human or animal body because its spectral luminance profile (range of 3-7 µm and peak wavelength at 4 µm) corresponds to the IR absorption of water (at 2.87, 3.05, 3.65, and 6.08 µm), and also most "Functional Groups" as disclosed before. Of course, additional samples may be produced with wt. % that vary from Samples 1 and 2 disclosed herein. Those alternate compositions are considered to be within the scope of the invention.

In a preferred embodiment of the present invention, the therapeutic device comprises IR-emitters in two different wavelength bands to enhance overall FIR activation effect on molecules in body fluids and thus magnify the health benefits. In particular, the array contains two types of IR-emitting ceramic elements that have different ceramic compositions. In one embodiment, the array comprises ten ceramic elements, six of which have the composition of Sample-1 and four of which have the composition of Sample-2. It is apprehended that more than two sets of ceramic elements may be used, and the elements may be distributed in different patterns, and different relative quantities and locations in the array.

In experiments, the ceramic samples are made into a shape of ⅓-circumference cutout of a 12-mm long cylindrical tube, with 15-mm I.D. (inner diameter) and 30-mm O.D. (outer diameter). All Samples-1 and Samples-2 are arranged in an array formation as shown in FIG. 1 and secured with polysulfide rubber mold compound. The concave side is arranged to face toward the body to be treated. A penetration depth of about 1 inch into the body is anticipated. The FIR photons absorbed by the body are expected to be carried around through the body by blood circulation. In some of the cases a heating device may be desired. Encouraging results with the device of present invention have been observed.

CONCLUSION, RAMIFICATIONS, AND SCOPE

According to the present invention, a therapeutic device comprises an array of IR-emitting elements in an attachment means, said IR-emitting element being an IR-emitting ceramic plate made of a mixture of IR-emitting oxides having specific spectral luminance covering at least a part of 3-14 µm (micrometer) wavelength spectrum, and more specifically, said array comprising at least first and second infrared-emitting elements, the first infrared-emitting element being a first ceramic plate comprising a first mixture of infrared-emitting oxides, the first infrared-emitting ceramic element having a first specific spectral luminance covering at least a part of the 3-7 micrometer wavelength spectrum, the second infrared-emitting element being a second ceramic plate comprising a second mixture of infrared-emitting oxides, the second infrared-emitting ceramic element having a second specific spectral luminance covering at least a part of the 7-14 micrometer wavelength spectrum, the second specific spectral luminance being different from the first specific spectral luminance and the second peak wavelength being different from the first peak wavelength, for providing an effective means to healing human or animal body.

The invention has been described above. Obviously, numerous modifications and variations of the present invention are possible in light of the above teachings. Such variations are not to be regarded as a departure from the spirit and scope of the invention and all such modifications as would be obvious to one skilled in the art are intended to be included within the scope of the following claims.

The invention claimed is:

1. A therapeutic device for attachment to a human or animal body, comprising: a flexible substrate, an array of infrared-emitting ceramic elements disposed on or within the substrate, with each ceramic element including a concave surface oriented towards the human or animal body part to be treated when the device is attached to the human or animal body part to be treated, and an attachment means, the array comprising at least a first plurality of infrared-emitting ceramics element having a first specific spectral luminance covering the wavelength range of 3-7 µm and a first peak wavelength within the range of 3-7 µm, and at least a second infrared-emitting ceramic element having a second specific spectral luminance covering the wavelength range of 7-14 µm and a second peak wavelength within the range of 7-14 µm, wherein the first specific spectral luminance is different from the second specific spectral luminance, and wherein the first peak wavelength is different from the second peak wavelength.

2. The therapeutic device according to claim 1, wherein the flexible substrate is comprised of silicone, zinc sulfide, sodium chloride, potassium bromide, or rubber.

3. The therapeutic device according to claim 2, wherein the flexible substrate is comprised of rubber, and wherein the array of infrared-emitting ceramic elements are embedded within the flexible substrate.

4. The therapeutic device according to claim 2, wherein each of the infrared-emitting ceramic elements are attached to an exterior surface of the flexible substrate using wires or strings.

5. The therapeutic device according to claim 1, wherein the infrared-emitting ceramic element is shaped as a hemisphere, a bowl, or a partial cylinder.

6. The therapeutic device according to claim 5, wherein each infrared-emitting ceramic element is shaped as a partial cylindrical tube having a diameter of 2-50 mm and a thickness of 1-20 mm.

7. The therapeutic device according to claim 5, wherein each infrared emitting ceramic element is shaped as a ⅓-circumference cutout of a 12 mm long cylindrical tube, having an outer diameter of 30 mm and an inner diameter of 15 mm.

8. The therapeutic device according to claim 1, further comprising an infrared reflecting means disposed on or within the flexible substrate and positioned such that the array of infrared-emitting ceramic elements is positioned between the infrared reflecting means and the human or animal body part to be treated.

9. The therapeutic device according to claim 8, wherein the infrared reflecting means is a metallic film, sheet, mesh, or coating.

10. The therapeutic device according to claim 1, wherein the first specific spectral luminance has a first minimum wavelength ($\lambda_1$) and a first maximum wavelength ($\lambda_2$) and the second specific spectral luminance has a second minimum wavelength ($\lambda_1$) and a second maximum wavelength ($\lambda_2$), and wherein the first minimum wavelength and first maximum wavelength are both within the range of 3-7 μm and the second minimum wavelength and second maximum wavelength are both within the range of 7-14 μm.

11. The therapeutic device according to claim 10, wherein the first minimum wavelength is 3 μm, the first maximum wavelength is 7 μm, and the first peak wavelength is 4 μm.

12. The therapeutic device according to claim 10, wherein the second minimum wavelength is 7 μm, the second maximum wavelength is 14 μm, and the second peak wavelength is 7 μm.

13. The therapeutic device according to claim 1, wherein each of the infrared-emitting ceramic elements comprise at least one infrared emitting oxide selected from the group consisting of: silicate, alumina, zirconia, sodium monoxide, potassium oxide, ferric oxide, chromic oxide, cobalt oxide, magnesium oxide, lithium oxide, calcium oxide, and titanium oxide.

14. The therapeutic device according to claim 13, wherein each of the infrared-emitting ceramic elements further comprise 5-40 wt. % tourmaline.

15. The therapeutic device according to claim 14, wherein each infrared-emitting ceramic element of either the first or second pluralities of infrared-emitting ceramic elements comprise 20 wt. % silicate, 20 wt. % alumina, 24 wt. % zirconia, 4 wt. % sodium monoxide, 3 wt. % potassium oxide, 3 wt. % ferric oxide, 5 wt. % chromic oxide, 4 wt. % cobalt oxide, and 15% tourmaline, wherein the remaining 2 wt. % comprises other metal oxides.

16. The therapeutic device according to claim 14, wherein the each infrared-emitting ceramic element of the first plurality of infrared-emitting ceramic elements comprises 20 wt. % silicate, 20 wt. % alumina, 24 wt. % zirconia, 4 wt. % sodium monoxide, 3 wt. % potassium oxide, 2 wt. % ferric oxide, 4 wt. % chromic oxide, 3 wt. % cobalt oxide, and 3% nickel oxide.

17. The therapeutic device according to claim 14, wherein the each infrared-emitting ceramic element of the second plurality of infrared-emitting ceramic elements comprises 20 wt. % silicate, 20 wt. % alumina, 24 wt. % zirconia, 4 wt. % sodium monoxide, 3 wt. % potassium oxide, 5 wt. % ferric oxide, 5 wt. % chromic oxide, and 2 wt. % cobalt oxide.

18. A method for treatment of a human or animal body part, comprising:
   a) providing an array of infrared-emitting elements disposed on or within a flexible substrate for attaching the array to the body part to be treated, the array comprising at least a first plurality of infrared-emitting ceramics element having a first specific spectral luminance covering the wavelength range of 3-7 μm and a first peak wavelength within the range of 3-7 μm, and at least a second infrared-emitting ceramic element having a second specific spectral luminance covering the wavelength range of 7-14 μm and a second peak wavelength within the range of 7-14 μm, wherein each ceramic element includes a concave surface oriented towards the human or animal body part to be treated when the device is attached to the human or animal body part to be treated, and wherein the first specific spectral luminance is different from the second specific spectral luminance, and wherein the first peak wavelength is different from the second peak wavelength;
   b) attaching the array of infrared-emitting elements to the body part; and
   c) irradiating the body part with infrared radiation emitted by the infrared-emitting ceramic elements.

19. The method according to claim 18, further comprising heating the infrared-emitting elements with a heating element to achieve escalated healing effects.

\* \* \* \* \*